United States Patent [19]

Falls

[11] Patent Number: 4,567,370

[45] Date of Patent: Jan. 28, 1986

[54] AUTHENTICATION DEVICE

[75] Inventor: James J. Falls, Salem, N.H.

[73] Assignee: Baird Corporation, Bedford, Mass.

[21] Appl. No.: 581,582

[22] Filed: Feb. 21, 1984

[51] Int. Cl.$^4$ .............................................. G01N 21/64
[52] U.S. Cl. ................................................ 250/461.1
[58] Field of Search ................... 250/458.1, 461.1, 302; 283/92

[56] References Cited

U.S. PATENT DOCUMENTS

| | | | |
|---|---|---|---|
| 3,663,813 | 5/1972 | Shaw | 250/461.1 |
| 4,127,773 | 11/1978 | West | 250/461.1 |
| 4,146,792 | 3/1979 | Stenzel et al. | 250/461.1 |
| 4,451,521 | 5/1984 | Kaule et al. | 250/461.1 |
| 4,451,530 | 5/1984 | Kaule et al. | 250/461.1 |

Primary Examiner—Janice A. Howell
Attorney, Agent, or Firm—Morse, Altman & Dacey

[57] ABSTRACT

An authentication device for various items is disclosed. The authentication device includes a sample treated with at least two luminophors, each luminophor being ultra-violet energy excitable but one emitting in the visible and the other in the infrared spectral range, an excitation lamp to excite the treated sample, a pair of detectors one each for detecting radiation in the visible and in the infrared spectral range, a source of power, and a display coupled to the pair of detectors. Preferably, the authentication device is provided with an optional multi-channel fiber optic cable. Preferably, the authentication device is light and portable. Preferably, the source of power is a battery. Preferably, the battery is rechargeable.

11 Claims, 5 Drawing Figures

AUTHENTICATION DEVICE

BACKGROUND OF THE INVENTION

1. Field of the Invention

The present invention relates generally to security and encoding techniques and, more particularly, to an authentication device for various types of goods, including papers, inks, plastics, metals, ceramics and the like.

2. The Prior Art

Authentication of stolen or lost items, including paintings as by the masters, has always represented a tedious process, requiring painstaking examination by experts. And even the experts have been proven incorrect at times. Authentication of legitimate paper currency from counterfeit also is not within the purview of most people required to handle the same. And authentication of stock and bond certificates, particularly of bearer bonds of high denominations, can cause troublesome delays to all concerned. Despite the time and effort expended during a thorough examination, the experts nevertheless have proved to be wrong at times, with attendant loss to some and embarrassment to others. With the advent and widespread use of security badges required to gain access to classified areas, the telling of the real from the fake, particularly on-the-spot and without undue delay, has become a challenge indeed. For, long delays in authentication serve to defeat one purpose of a security badge, namely the admission of authorized personnel only, but quickly and without delay.

Present day security and encoding techniques employ, among others, the use of fluorescent materials. When applied to a flat object, these materials are excitable, hence readable, at their respective characteristic wavelengths. Sophisticated thieves of high value paintings and bearer bonds, as well as espionage experts, have managed to overcome and thus "fool" even these safeguards.

Hence, there is a continuing need constantly to improve security and encoding techniques and design a more foolproof system, one which nevertheless allows quick, on-the-spot verification, yet with a high degree of reliability.

SUMMARY OF THE INVENTION

It is a principal object of the present invention to overcome the above disadvantages by providing an authentication device for items such as security papers, inks, plastics, metals, ceramics and the like.

More specifically, it is an object of the present invention to provide an authentication device comprising a sample treated with phosphors which emit, when excited by an intense, short wavelength, ultra-violet radiation source, at different spectral range levels, an excitation source to excite the treated sample, a pair of detectors for detecting emitted radiation at those different levels, a source of power coupled to the excitation source, and a display coupled to the pair of detectors. Preferably, the authentication device is provided with an optional multi-channel fiber optic cable to verify unusually-shaped products. Preferably, the authentication device is light and portable. Preferably, the source of power is a battery. Preferably, the battery is rechargeable. Preferably, the display includes both a visible and an audible signal indicator. The phosphors can be incorporated into paper, ink, plastics, metals and ceramics during their manufacture, or they can be poured onto the surface of the material to be encoded in the form of a slurry. The phosphors also can be applied onto the materials by spraying, or phosphor precoated strips or discs can be fastened thereto.

Other objects of the present invention will in part be obvious and will in part appear hereinafter.

The invention accordingly comprises the authentication device of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF THE PREFERRED EMBODIMENT

Figure 1:
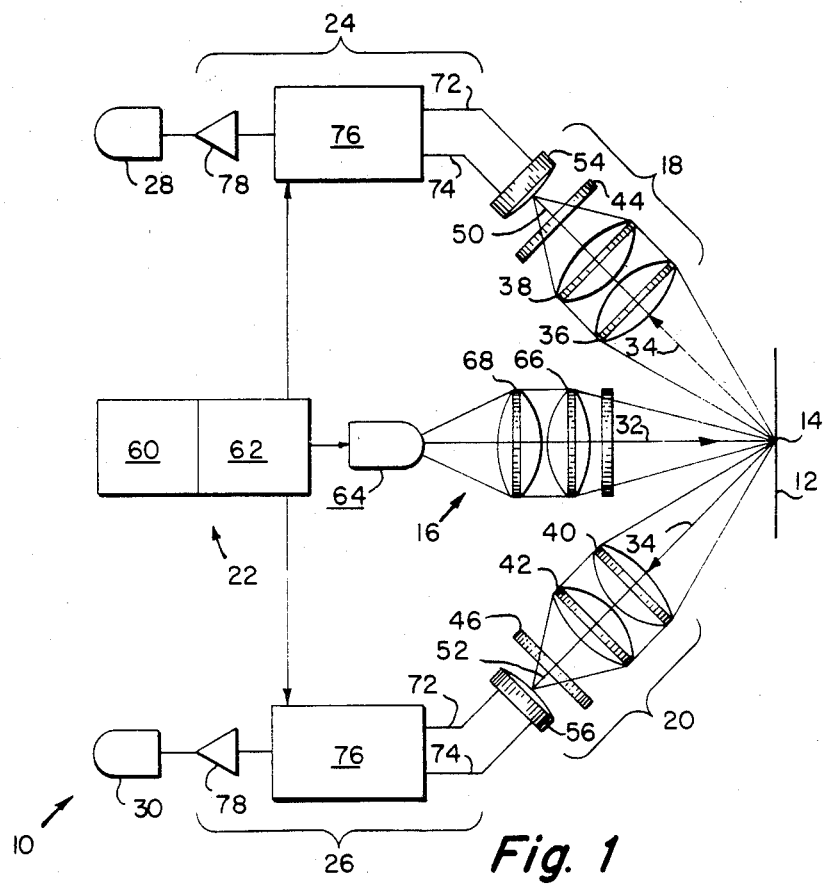
FIG. 1 is a schematic representation of an authentication device constructed in accordance with the present invention.

In general, the illustrated embodiment of an authentication device 10 comprises a sample 12, treated at a target area 14 with at least two luminophors, each excitable in the ultra-violet range but emitting at a different, spectral range level, an excitation source 16 to excite the treated sample 12, a pair of detectors 18 and 20 for detecting radiation emitted at the different spectral range levels, a source of power 22 for the excitation source 16, processing electronics 24 and 26 coupled to the pair of detectors 18 and 20, and a display unit 28 and 30 coupled to the processing electronics 24 and 26.

The treated (i.e., encoded) sample 12 may include one of the following products, or the like:

| Paper-based products | |
| --- | --- |
| Currency | Drug Labels |
| Stock Certificates | Phonograph Labels/Jackets |
| Bonds | Video Cassette Labels/Packaging |
| Checks | Inspection Stickers |
| Titles | Licenses |
| Lottery Tickets | Credit Cards |
| Sports/Theater Tickets | I.D. Cards |
| Airline Tickets | Food Stamps |
| Important Receipts | Tax Stamps |
| Proprietary Drawings | Books |
| Confidential Memoranda | Gift Certificates |
| Apparel Labels | Software Printouts |
| Paintings | |
| Other Products | |
| Magnetic Tapes | Security Badges |
| Records | Computer Discs |
| Electronic Components | Drug Containers |
| Aircraft Components | Most Plastic Materials |
| Auto Parts | Most Glass Containers |
| Films | Most Ceramic Materials |
| Microfilm | Inks |

-continued

Paints

The target area 14 of the sample 12 need not be large and typically is a spot of about ten millimeters. The operator of the authentication device 10, of course, will need to know where the treated target area 14 of the sample 12 is, particularly if the size of the sample 12 is large. For, otherwise the entire area of the sample 12 will have to be scanned. The target area 14 of the sample 12 preferably is treated with at least two luminophors, each of which being excitable at one energy level but emitting at different spectral range levels. By the term "luminophor" as used in this specification and in the appended claims, it is meant to define a luminescent material that converts part of the absorbed primary energy into emitted luminescent radiation. Preferably, each of the two luminophors is a different kind of a powdered phosphor, diluted with a suitable vechicle, such as an aquaous sizing solution. Preferably, the resultant paste of powdered phosphors and diluent is applied to the target area 14 of the sample 12 as by spraying or coating, using a transparent vehicle, or in an ink or paint. A major feature of all the phosphors and vehicles used is the fact that they are transparent and not visible after application.

Alternatively, the phosphors can be incorporated into paper, ink, plastics, metals, and ceramics during their manufacture. The phosphors in no way alter the appearance, weight, or useful life of the end product. Or the phosphors can be deposited into the papers, plastics, metals, or ceramics in a pattern of single or multiple stripes. Or the phosphors can be poured onto the surface of the material to be encoded in the form of a slurry or can be applied onto the material via a thin support in the form of a strip or discs (such as planchets), and attached or otherwise secured to the material.

Each of the luminophors used is excitable by ultraviolet radiation below the 200 nanometer range, that is way below the conventional black light. Normal "black light" ultraviolet sources do not have much intensity in the short wavelength region (200 to 300 nanometers) to excite phosphors. These sources also have considerable visible emission which will mask the fluorescence. Once excited however, each of the two luminophors emits characteristic radiation at widely different spectral range levels: with one luminophor emitting in the visible range, preferably at 625 nanometers; and the other luminophor emitting in the infrared range, preferably at 875 nanometers. For example, phosphor HGE 496 emits in the visible range and phosphor HGE 497 emits in the infared range.

The working principle of the invention is best described with reference to FIG. 1. Ultra-violet radiation 32 emanating from the excitation source 16 strikes the treated target area 14 of the sample 12 and excites the two luminophors with which the target area 14 previously had been treated. As a result of this ultra-violet excitation, the two luminophors begin to emit from the target area 14 radiation 34 that contains the characteristic emitted radiations of both luminophors, that is radiation both in the visible range, preferably at 625 nanometers, and in the infrared range, preferably at 875 nanometers. After focusing by a pair of lenses 36, 38 and 40, 42, the emitted radiation 34 respectively is filtered by interference filters 44 and 46 before the selected characteristic radiations 50 and 52 are permitted to strike the respective detector elements 54 and 56 of the pair of detectors 18 and 20. Preferably, the detector elements 54 and 56 are silicon diode detectors. The selected characteristic radiations 50 and 52 are, of course, the respectively emitted characteristic radiations of the two luminophors. One is in the visible and the other in the infrared range, i.e., one at the preferred 625 nanometers and the other at the preferred 875 nanometers. Should one or both of these selected characteristic radiations 50 and 52 be absent or of different wavelengths, one or both of the respective displays 28 and 30 becomes actuated, indicating a "fail" for the just measured sample 12. Such "fail" preferably is indicated both by a flashing light in the respective display units 28 and 30 and by an audible sound, alerting the operator, all forming a part of the display units 28 and 30 as is well known to those skilled in the art.

The preferred source of power 22 is a light-weight rechargeable battery 60, such as a cadmium-zinc battery. The power source 22 powers both the excitation source 16 as well as the processing electronics 24 and 26 and therethrough the respective display units 28 and 30. Consequently, a suitable transformer unit 62 is connected respectively between the battery 60 and the excitation source 16 on the one hand and between the battery 60 and the processing electronics 24 and 26 so as to supply the respective different power requirements to these units.

The excitation source 16 essentially includes a suitable lamp 64, a pair of focusing lenses 66 and 68, and a filter 70. The lamp 64 preferably is a short-lighted length, Vycor glass jacketed mercury vapor lamp. Vycor glass is a nearly pure silicon glass formed from a soda borosilicate glass as opposed to fused silica. As known, the Vycor glass jacket of the lamp 64 serves to suppress ozone interference, and thus improve the reliability of the authentication device 10 in which it is used. The pair of focusing lenses 66 and 68 preferably are quartz lenses, and the preferred filter 70 is a mercury filter designed to reduce the ultra-violet radiation, generated by the lamp 64 and focused by the lenses 66 and 68, to a spectral range level below the 200 nanometer wavelength. The processing electronics 24 and 26 respectively comprise appropriate electrical connections, such as the pair of wires 72 and 74, a band pass filter 76, and a suitable amplifier 78.

Figure 2:
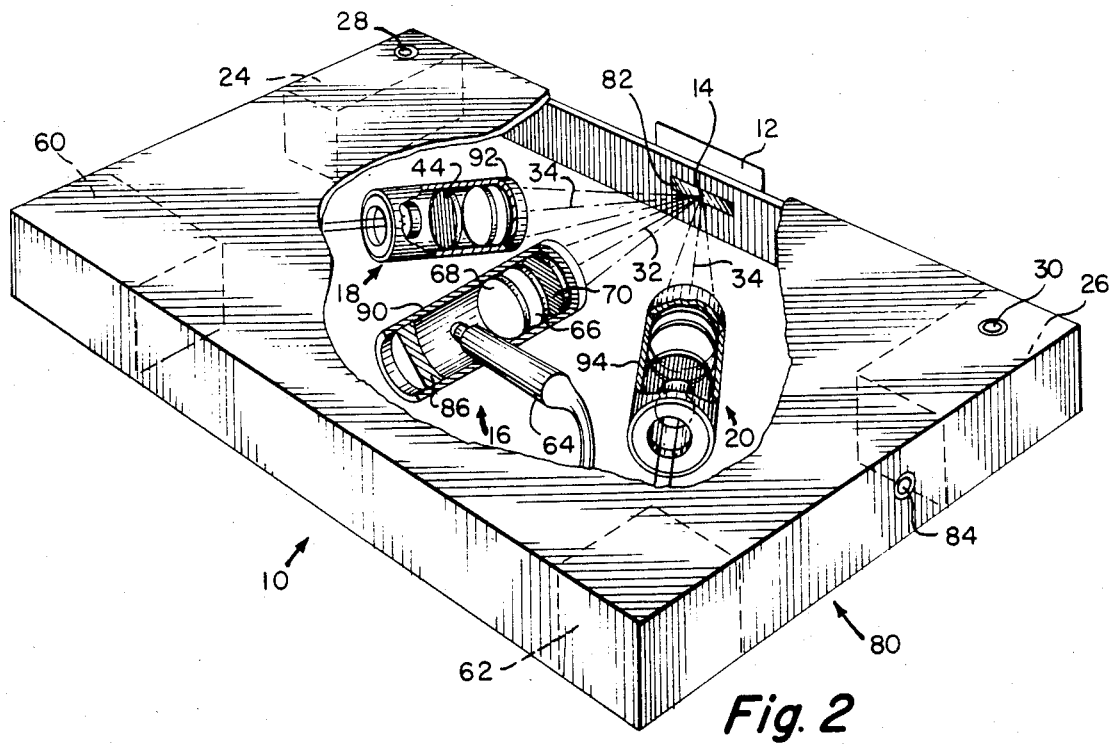
FIG. 2 is a perspective schematic view, with parts broken away, of the authentication device of the invention.

The above-enumerated components of the authentication device 10 preferably are contained within a compact housing 80, observe FIG. 2. Preferably, the repective dimensions of the housing 80 do not exceed 8"×6"×3", and could even be somewhat less. Preferably, the housing 80 is made of a suitable light-weight material, such as wood, hard-plastic, or a combination thereof. At one side of the housing 80, there is provided a slot 82. It is against this slot 82 that the treated target area 14 of the sample 12 is laid or held during the authentication process itself. An actuating member 84, such as a button or the like, also is provided on a side of the housing 80, preferably at a location most convenient to the operator of the device 10. A suitable outlet, not shown, also is provided in the housing 80 for connection to a conventional 110 VAC power supply to recharge the battery 60. Of course, each of the operative parts of the authentication device 10, such as the excitation source 16, the pair of detectors 18 and 20, the battery 60 and the transformer unit 62, is appropriately secured within and to the housing 80 by suitable known fastener means, not shown. The excitation source 16 preferably also includes a reflective element 86 designed to intensify the radiation generated by the lamp 64 and to direct the intensified radiation toward the pair of focusing lenses 66 and 68. Preferably the reflective element 86 is a concave mirror. Further, the excitation source 16 and the pair of detectors 18 and 20 are all enclosed in their respective individual housings, such as tubes 90, 92 and 94, respectively.

Figure 4:
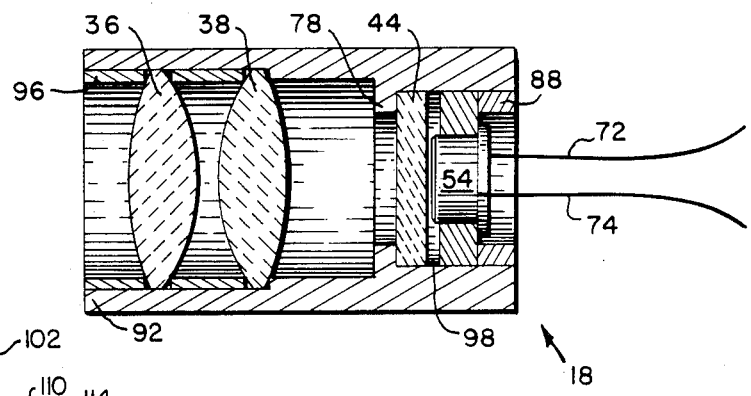
FIG. 4 is a sectional view, on an enlarged scale, of one operative part of the authentication device shown in FIG. 2.

A detailed sectional view of one 18 of the pair of detectors 18 and 20 is disclosed in FIG. 4. The pair of lenses 36 and 38 preferably are made of glass, as opposed to the quartz lenses 66 and 68 of the excitation source 16. The lenses 36 and 38 preferably are removeably mounted in the free end of the tubular housing 92 by means of a suitable sleeve member 96 secured therein in any known conventional manner. The interference filter 44 and the detector element 54 are removeably secured within the other end of the tubular housing 92 by means of a spacer ring 98 and a mounting sleeve 88. The housing 92 is formed with an integral divider 78 against which rests the interference filter 44, as shown. The other one 20 of the pair of detectors 18 and 20 is in all respects identical and interchangeable with the one 18 shown in and described with reference to FIG. 4.

Figure 5:
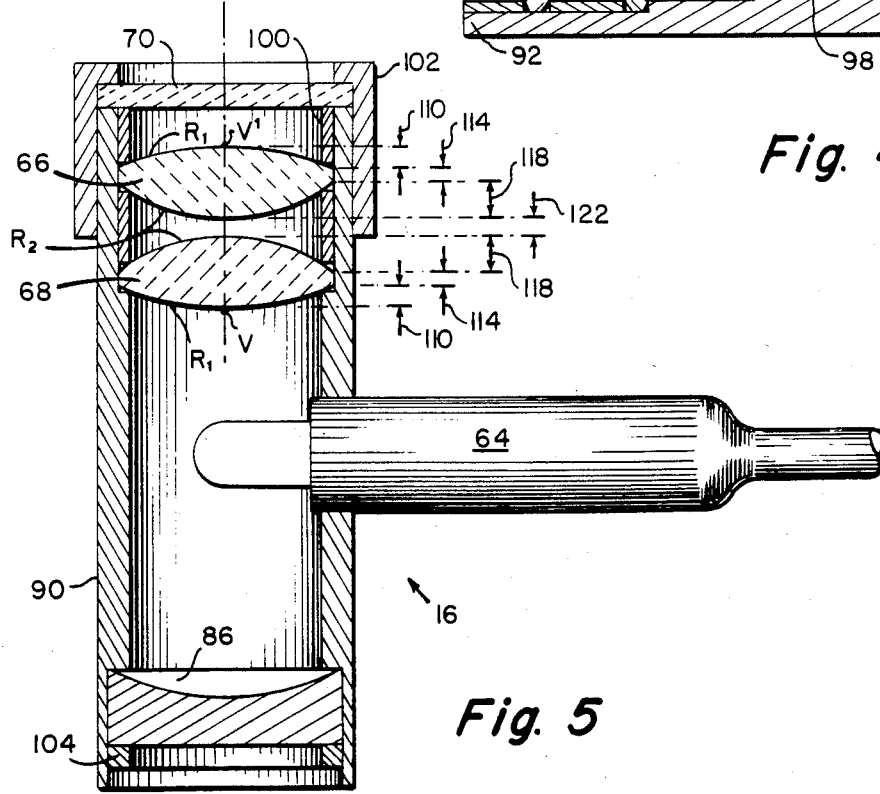
FIG. 5 is a sectional view, on an enlarged scale, of another operative part of the authentication device shown in FIG.2.

A detailed sectional view of the excitation source 16 is disclosed in FIG. 5. The pair of quartz focusing lenses 66 and 68 also are mounted in the free end of the tubular housing 90 by means of a sleeve member 100, but this time behind the filter 70. The filter 70 itself preferably is secured in place by a member 102, which is secured onto the outer free end of the tubular housing 90, much like the cover in a hand-held flashlight. The reflective element 86 removably is secured in the other end of the tubular housing 90 via a retainer ring 104.

Although the lenses 36, 38 and 40 and 42 preferably are made of glass and the lenses 66 and 68 preferably are made of quartz, the following specifications, noted with respect to the lenses 66 and 68 in FIG. 4, apply to all of them.

$R_1 = -28.96$ mm; $R_2 = 45.80$ mm; $t_{ax} = 11.36$ mm; and $VV^1 = 23.3$ mm. This latter dimension between the vertexes $VV^1 = 23.3$ mm, adds up as follows: twice the distance represented by the arrows $110 = 3.5$ mm, twice the distance represented by the arrows $114 = 2.0$ mm, twice the distance represented by the arrows $118 = 5.9$ mm, and the distance represented by the arrow 122 separating the lenses $= 0.5$ mm.

The effective focal length (EFL) of the pair of quartz lenses 66 and 68, as measured in yellow light, is 22.2 mm, and the back focal length (BF) of these lenses 66 and 68 is 12.9 mm. The effective focal length of the glass lenses 36, 38 and 40, 42, on the other hand, is 19.9 mm, with the back focal length being 11.0 mm, also measured in yellow light.

The index of refraction ($n_D$) for each of the quartz lenses 66 and 68 is 1.4584. The index of refraction for each of the glass lenses 36, 38 and 40, 42, on the other hand, is 1.5162, also measured in yellow light.

Figure 3:
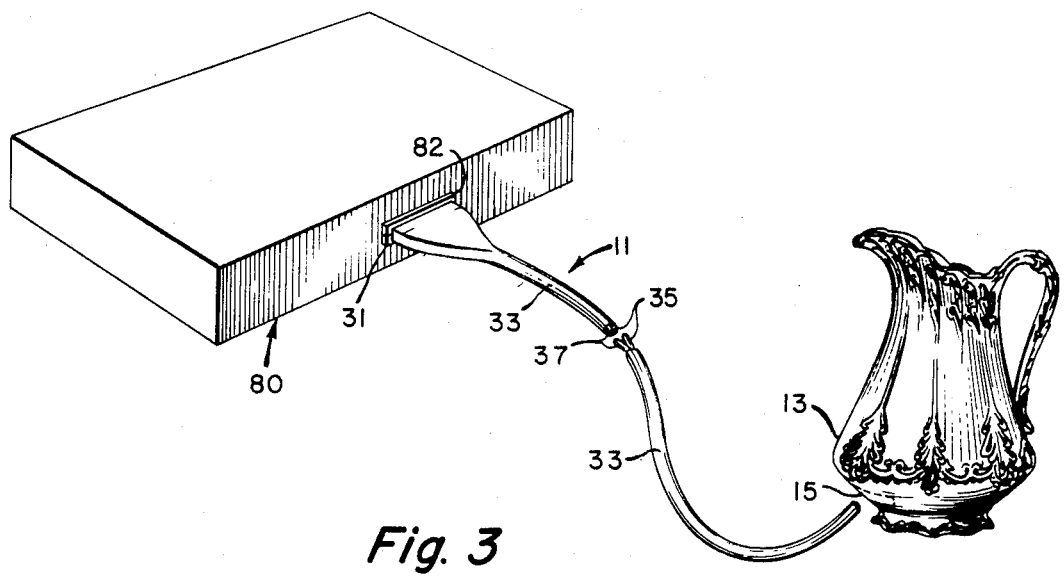
FIG. 3 is a perspective of the authentication device of FIG. 2 but showing its use with an optional accessory.

Some treated samples, such as bottles, phonograph labels, books, magnetic tapes, aircraft or auto components, computer discs, ceramic materials and the like, do not lend themselves to be positioned adjacent the slot 82 of the authentication device 10. In order to adapt the device 10 also to verify the authenticity of such products, an optional accessory 11 preferably is provided for use with the device 10. The optional accessory 11 and its use on a sample 13, such as a decanter, are depicted in FIG. 3. The sample 13 also is provided with a treated target area 15, which may be a label, a strip or disc or the like and attached or otherwise secured to the sample 13. The target area 15 also can be formed as by spraying or coating a slurry of the luminophors thereon at that spot; or the target area 15 can be formed during the manufacture of the particular sample 13 itself.

The optional accessory 11 essentially comprises a flexible multi-channel fiber optic cable 33 provided at one end with an attachment 31 that can be removably fitted over the slot 82 of the housing 80, as by snap-fitting. The fiber optic cable 33 comprises one set of fiber optic bundles 35 designed to pick up the ultra-violet radiation 32 generated by the excitation source 16 and to carry it to the treated target area 15 so as to excite the luminophors thereat, and another set of fiber optic bundles 37 designed to pick up the emitted radiation 34 generated by the ultra-violet radiation 32 from the target area 15 and to transmit the same to the pair of detectors 18 and 20. It will be appreciated that the length of the fiber optic cable 33 can be any convenient length from a few feet to several yards. Further, the authentication device 10 can be provided with more than one such accessory 11, one featuring a short-length cable 33, another a medium-length cable 33, and still another a long-length cable 33. Because of the snap-fit of the attachment 31 over the slot 82, the cables 33 can be easily exchanged or removed.

Thus it has been shown and described an authentication device 10 designed for the quick, on-the-spot verification of treated items, which device 10 satisfies the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. An authentication device comprising:
(a) a sample treated with at least two luminophors each being ultra-violet energy excitable but emitting radiation at different spectral ranges;
(b) an excitation source to excite said treated sample;
(c) a pair of detectors for detecting said emitted radiation at said different spectral ranges; and
(d) a source of power coupled to said excitation source;
(e) said luminophors being each excitable by radiation at wavelength below 200 nanometers;
(f) one of said luminophors emitting in the visible range and the other of said luminophors emitting in the infrared range.

2. The authentication device of claim 1 wherein said sample comprises one of the following materials: papers, inks, plastics, metals, ceramics or a combination of the above materials.

3. The authentication device of claim 1 wherein said luminophors are each different combinations of powdered phosphors diluted with a vehicle and applied on a target area of said sample.

4. The authentication device of claim 1 further including an accessory comprising a flexible multi-channel fiber optic cable coupled between said excitation source and said sample and between said sample and said pair of detectors.

5. The authentication device of claim 1 wherein said one of said luminophors emits at a wavelength of about 625 nanometers and the other of said luminophors emits at a wavelength of about 875 nanometers.

6. An authentication device comprising:

(a) a sample treated with at least two luminophors each being ultra-violet energy excitable but emitting radiation at different spectral ranges;

(b) an exciatation source to excite said treated sample;

(c) a pair of detectors for detecting said emitted radiation at said different spectral ranges;

(d) a source of power coupled to said excitation source;

(e) said luminophors being each different combinations of powdered phosphors diluted with a vehicle and applied on a target area of said sample;

(f) said excitation source comprising a short-length, Vycor glass jacketed mercury vapor lamp emitting ultra-violet radiation, a reflective element designed to intensify said ultra-violet radiation, a focusing element designed to focus said intensified ultra-violet radiation on said target area of said sample, and a filter to reduce said focused intensified ultra-violet radiation to a spectral range below 200 nanometers;

(g) said reflective element being a concave mirror, said focusing element comprising a pair of quartz lenses, and wherein said lamp is mounted at an angle normal to the optical axis of said pair of quartz lenses.

7. The authentication device of claim 6 wherein each of said pair of detectors comprises a detector element, a filter, and a focusing element designed to focus said emitted radiation at said different spectral ranges at said detector element; wherein one of said filters is designed to admit radiation emitted at a wavelength of about 625 nanometers and the other of said filters is designed to admit radiation emitted at a wavelength of about 875 nanometers; and wherein said focusing element of each of said pair of detectors comprises a pair of glass lenses, and wherein said detector element of each of said pair of detectors is a silicon diode detector.

8. The authentication device of claim 6 wherein said pair of quartz lenses have an $R_1$ of $-28.96$ mm, and an $R_2$ of 45.08 mm; and wherein said pair of quartz lenses have an effective focal length of 22.2 mm and a back focal length of 12.9 mm, measured in yellow light.

9. The authentication device of claim 6 wherein said pair of glass lenses have an $R_1$ of $-28.96$ mm, and an $R_2$ of 45.80 mm.

10. An authentication device comprising:

(a) a sample treated with at least two luminophors each being ultra-violet energy excitable but emitting radiation at different spectral ranges;

(b) an excitation source to excite said treated sample;

(c) a pair of detectors for detecting said emitted radiation at said different spectral ranges;

(d) a source of power coupled to said excitation source;

(e) one of said luminophors emitting in the visible range and the other of said luminophors emitting in the infrared range;

(f) a housing provided with a slot for said sample and a display coupled to said pair of detectors, wherein said source of power is a battery;

(g) said display comprising both a visual and an audible portion to indicate a pass or a fail condition for said sample; and (h) a connecting cable, a band pass filter and an amplifier by which each of said pair of detectors is coupled to said display.

11. The authentication device of claim 10 which is portable and wherein said battery is rechargeable.

* * * * *